(12) United States Patent
Wyman et al.

(10) Patent No.: US 8,795,830 B2
(45) Date of Patent: Aug. 5, 2014

(54) PRIMER FOR COATING COILED WIRES

(75) Inventors: Paul Wyman, Maastricht (NL); de Nik Bont, Stein (NL); Hinrike Malda, Rosmalen (NL); Mamix Rooijmans, Born (NL); Jurgen Scheerder, Buren (NL); Rajasingham Satgurunathan, Voorschoten (NL); Thomas L. M. Frijns, Heerlen (NL)

(73) Assignee: DSM IP Assets B.V., Heerlen (NL)

( * ) Notice: Subject to any disclaimer, the term of this patent is extended or adjusted under 35 U.S.C. 154(b) by 104 days.

(21) Appl. No.: 13/143,791

(22) PCT Filed: Jan. 11, 2010

(86) PCT No.: PCT/EP2010/050232
§ 371 (c)(1),
(2), (4) Date: Oct. 27, 2011

(87) PCT Pub. No.: WO2010/079229
PCT Pub. Date: Jul. 15, 2010

(65) Prior Publication Data
US 2012/0041545 A1    Feb. 16, 2012

(30) Foreign Application Priority Data
Jan. 9, 2009    (EP) .................................... 09150344

(51) Int. Cl.
*C09D 5/00* (2006.01)
*C09D 153/00* (2006.01)
*A61L 31/10* (2006.01)

(52) U.S. Cl.
USPC ......... 428/364; 427/409; 427/2.1; 427/388.1; 427/388.4

(58) Field of Classification Search
USPC ........ 427/407.1, 2.1–2.31, 409, 388.1, 388.4; 428/364
See application file for complete search history.

(56) References Cited

U.S. PATENT DOCUMENTS

| | | | | |
|---|---|---|---|---|
| 5,266,359 A | * | 11/1993 | Spielvogel | 427/388.4 |
| 5,756,144 A | * | 5/1998 | Wolff et al. | 427/2.3 |
| 6,030,656 A | * | 2/2000 | Hostettler et al. | 427/2.3 |
| 6,221,425 B1 | * | 4/2001 | Michal et al. | 427/2.25 |
| 7,244,783 B2 | * | 7/2007 | Lean et al. | 524/505 |
| 2003/0199964 A1 | | 10/2003 | Shalaby et al. | |
| 2005/0147647 A1 | | 7/2005 | Glauser et al. | |
| 2007/0269480 A1 | | 11/2007 | Richard et al. | |
| 2008/0306455 A1 | | 12/2008 | Dias et al. | |

FOREIGN PATENT DOCUMENTS

| | | |
|---|---|---|
| JP | 2002-501788 | 1/2002 |
| JP | 2004-565 | 1/2004 |
| JP | 2004-000565 A2 * | 1/2004 |
| WO | 99/35846 | 8/1999 |
| WO | 99/38545 | 8/1999 |

OTHER PUBLICATIONS

International Search Report for PCT/EP2010/050232, mailed May 7, 2010.
Written Opinion for PCT/EP2010/050232, mailed May 7, 2010.
JP Office Action with English-language translation dated Dec. 3, 2013.

* cited by examiner

*Primary Examiner* — William Phillip Fletcher, III
(74) *Attorney, Agent, or Firm* — Nixon & Vanderhye P.C.

(57) ABSTRACT

Disclosed is a method to provide a metal wire with a coating system comprising a primer and a topcoat, particularly a hydrophilic, lubricious topcoat. The method comprises applying directly onto the wire metal a primer coating composition, which is an aqueous coating composition comprising a multiphase vinyl polymer, the polymer comprising a first phase having a Tg in the range of from −20° C. to 40° C. and a hard phase having a Tg in the range of from 25° C. to 120° C. The primer has good adhesion to both the metal surface and the topcoat, and provides the eventual coating system with, inter alia, a good flexibility.

16 Claims, No Drawings

PRIMER FOR COATING COILED WIRES

This application is the U.S. national phase of International Application No. PCT/EP2010/050232 filed 11 Jan. 2010 which designated the U.S. and claims priority to EP Patent Application No. 09150344.1 filed 9 Jan. 2009, the entire contents of each of which are hereby incorporated by reference.

FIELD OF THE INVENTION

The invention pertains to a primer for the coating of metal wires, especially coiled metal guidewires that may be used as a medical or surgical tool in the insertion of medical instruments into a body cavity. Particularly, the invention pertains to a primer to be combined with a curable topcoat, the curing of which results in a lubricious, hydrophilic surface.

BACKGROUND OF THE INVENTION

Medical instruments for insertion into body cavities find widespread use. These are e.g. catheters, electrodes, sensors, imaging aids and guide wires that are inserted through trachea, blood vessels, urethra or other celoms or tissues.

Such instruments are required to have a high degree of smoothness to assure introduction thereof into a body cavity or via another medical instrument without causing trauma to tissue encountered during placement and manipulation.

The use of inserted medical instruments may produce friction and abrasive forces that apply to the surfaces of the medical device. It is desirable for the frictional resistance between the medical device being inserted and it's contact surface, be it another device or the contact surface within a patient, to be low. Relatively high friction between, for instance, a catheter and a guide wire may not only inhibit the guide wire from being inserted through the catheter smoothly, but can also inhibit the easy movement of the guide wire through the catheter; making it more difficult to carry out subtle indwelling operations at, for instance, the destined blood vessel site.

Catheters typically consist of plastic tubes which may have a single lumen or multiple lumens. Catheters may have balloons fastened along the tube to obstruct a vessel or to fix the catheters in a desired position. Catheters may also have ports at the distal end, side ports along part of the length, or other mechanical features needed to accomplish the particular device's mission. Catheters may consist of a continuous length of tubing, or may comprise two or more sections of tubing consisting of similar or dissimilar materials which are welded together in order to have different properties at different locations along the length of the device. Catheters may be tapered, both within a segment or by having segments of differing diameters. Typical material of which catheters are constructed include polyamides, polyurethanes, polyvinyls such as polyvinylchloride, polyesters, polyolefins, silicones, and others. Typical diameters range from less than one millimeter to more than 8 millimeters.

As typically encountered in inserting a catheter, at the predetermined site, the guide wire tip is inserted through a catheter up to its tip opening, the catheter with the guide wire is inserted into, e.g., a blood vessel percutaneously, and the catheter is further inserted through the vessel by using the guide wire as a leading and supporting guide. These operations produce friction and abrasive forces that apply to the surfaces of the medical device. It is desirable for the frictional resistance between the catheter inner surface and the guide wire to be low. Relatively high friction between the catheter and the guide wire not only prevents the guide wire from being inserted through the catheter, but also prevents the guide wire from being easily moved through the catheter, making it difficult to carry out subtle indwelling operations at the destined vessel site. Sometimes the guide wire cannot be withdrawn from the catheter, rendering the catheter lumen unusable despite the completion of the indwelling operation.

To avoid such problems, attempts have been made in the art to apply low frictional resistance materials such as Teflon® or silicone oil to the outer surface of guide wires. Application of silicone oil fails to retain lubricity because of immediate loss of silicone coatings. Frequent applications add to frictional resistance, also undesirably creating troubles as mentioned above.

There is thus the need for a catheter and guide wire having a lower frictional resistance surface which enables more subtle operation in a blood vessel and can be easily inserted and remain at the site where catheters are otherwise difficult to manage during placement.

Polyurethane coatings have been applied directly on metal surfaces. A reference in this respect is U.S. Pat. No. 4,876,126. However, commercial versions of this technology require thick layers (60-80 microns thick) in order to perform adequately. In practice, the thick layer extends continuously around the coated metal substrate. These layers have good cohesive forces and thus appear to be tightly bound on the metal surface, even though these layers do not necessarily have good adhesion to the metal surface. A disadvantage of such coatings is that because the polyurethane and other plastic layers are so thick, the metal diameter of the underlying wire must be correspondingly diminished. This is especially troublesome on the very fine wires such as those used in cardiovascular medicine (e.g. in coronary angioplasty) or in neurointerventional catheterization procedures.

Illustrative wire and coiled wire diameters range from 200 microns to more than 2 millimeters in diameter, the total length of the wire or coiled wire containing device is commonly in the range of 50 cm to 2.5 m, the coiled part making up anywhere from 1 cm to the full length of the wire depending on the desired mechanical properties such as flexibility, torsional stability etc. All or only part of the device may require a coating.

Particularly in respect of coiled wires, it is however not simple to substitute a coating for the polyurethane jacket, as the requirements for such a coating are inevitably stringent. The coating should have sufficient elasticity to bend with the coiled wire and it should have sufficient adhesion to the metal. Also, it should be sufficiently wear-resistant to withstand the process of insertion.

Reference is made to WO 91/19756, which discloses a method for providing a metal wire with a lubricious, hydrophilic topcoat, wherein a two-layered coating is applied. The teaching of this reference is particularly directed to a process which involves applying a first latex coating, then applying a second coating, and ensuring that the first coating is not cured before the second is applied, after which both coatings are simultaneously cured with heat. The document seeks to provide coatings of sufficiently strong adhesion. It does not address the aforementioned more advanced set of desired properties. As the aforementioned heat curing process is of essence, the coated wires disclosed in the reference moreover are not applicable to low temperature curable, let alone radiation curable topcoats, to which the present invention particularly pertains.

All in all, it is desired to provide a method of coating metal wires suitable for insertion into a body cavity, particularly guidewires, and more particularly coiled wires, which satisfies one or more of the following: allowing a good adhesion of the coating to the metal wire; having a good intercoat adhesion, providing a surface of desirable lubricity; having a sufficient elasticity to accommodate coiled wires; having a sufficient wear-resistance to be used for insertion into a medical instrument, and provide the desired performance on the basis of a coating layer that is capable (e.g. by being not too thin) to conform to the coiled wire. Desirably, the coating is elastic enough not to break when the coil is bent, and is not deformed after bending.

In particular, it is desired to provide a primer for use in coating a metal surface, particularly a metal wire, with a coating comprising a curable topcoat, the curing of which results in a lubricious, hydrophilic surface, which primer exhibits a favorable combination of flexibility, elasticity, adhesion to the metal surface and adhesion to the topcoat. Desirably this results in an eventual coating on the metal that has a good intercoat adhesion and water resistance. Systems satisfying these combined properties are as yet unknown.

SUMMARY OF THE INVENTION

In order to better address one or more of the foregoing desires, the invention, in one aspect, is a method for coating a metal wire with a coating system comprising at least a primer and a topcoat, said topcoat being curable at less than 70° C., the method comprising:

I) applying directly onto the metal wire a primer coating composition, and allowing the primer to at least partially dry:

II) applying a topcoat coating composition;

III) curing the topcoat;

wherein the primer coating composition is an aqueous composition having a minimum film forming temperature of below 40° C., preferably below 30° C., comprising a multiphase vinyl polymer, comprising a first phase having a Tg in the range of from −20° C. up to 40° C., preferably −20° C. up to 25° C., and a second phase having a Tg in the range of from 25° C. to 120° C., preferably 40° C. to 120° C.; with the Tg of the second phase being higher than the Tg of the first phase.

In a further aspect, the invention pertains to the use of the foregoing primer composition for the coating of metal wires, and to the resulting coated metal wire, particularly coiled metal wires.

The invention, in yet another aspect, is a medical device comprising a coated metal wire, and such medical devices for use in cardiovascular medicine or in neurointerventional catheterization.

DETAILED DESCRIPTION OF THE INVENTION

The invention, in a broad sense, is based on the recognition that a coating composition comprising an aqueous emulsion of a multiphase vinyl polymer makes it possible to provide the right combination of properties for a primer in the coating of metal wires, particularly coiled wires.

The metal wires to which the invention is directed generally include all types of metal suitable for use in medical wire applications. These are known in the art and, preferably, comprise stainless steel (e.g. 304 and 316 grades), including passivated stainless steels or nickel/titanium alloys.

Multiphase vinyl polymer coatings are not normally used for such small-scale applications as the coating of guidewires. These are typically used in paints and varnishes, see e.g. WO 98/08882 or U.S. Pat. No. 5,731,377. The invention judiciously puts to use a recognition that the primer for a hydrophilic, lubricious topcoat, should combine several properties not normally obtained in a single coating composition, viz. adhesive, elastic, and cohesive properties.

According to the invention, this set of properties can be provided for by selecting an aqueous coating composition comprising a multiphase vinyl polymer.

By an aqueous coating composition is meant herein a dispersion or emulsion of the vinyl polymer in an aqueous carrier medium of which water is the principal component (at least 50% by weight, most usually at least 90% by weight of the carrier medium).

In the primer of the present invention, the balance between the Tg of the first and the second phase in the multiphase vinyl polymer is believed to be of importance.

The Tg of a polymer herein stands for the glass transition temperature and is well known to be the temperature at which a polymer changes from a glassy, brittle state to a rubbery state. Tg values of polymers may be calculated using the well-known Fox equation. Thus the Tg, in degrees Kelvin, of a copolymer having "n" copolymerised comonomers is given by the weight fractions W of each comonomer type and the Tg's of the homopolymers (in degrees Kelvin) derived from each comonomer according to the equation:

$$1/Tg = W_1/Tg_1 + W_2/Tg_2 + \ldots W_n/Tg_n.$$

The calculated Tg in degrees Kelvin may be readily converted to ° C.

A polymer having a Tg of −20° C. up to 40° C. is defined herein as a "soft" polymer, while a polymer having a Tg of 25° C. to 120° C. is defined herein as a "hard" polymer.

The difference in Tg between the at least two phases is preferably at least 20° C., more preferably at least 35° C. and most preferably 50° C. to 100° C.

Preferably, the multiphase vinyl polymer has a minimum film forming temperature of below 40° C., preferably below 30° C. and more preferably below 20° C.

In general the multiphase vinyl polymer will have more soft than hard polymer present. Thus, preferably, the soft polymer or, as the case may be, the soft portion of the polymer, will be present in a range of from 50 wt. % to 95 wt. % and the hard polymer or, as the case may be, the hard portion of the polymer, will be present in a range of from 5 wt. % to 50 wt. %. In multiphase polymers having more than two different phases, the total percentages of soft with respect to hard phases are preferably in line with the foregoing.

It will be understood that as the invention pertains to a coating composition, the multiphase vinyl polymers employed in the primer are suitable as coating compositions, i.e. they have film-forming properties. The person skilled in the art knows how to generally construct a vinyl polymer suitable for use in coating compositions.

By a vinyl polymer herein is meant a homo- or copolymer derived from the addition polymerisation (using a free radical process) of at least one olefinically unsaturated monomer which are also known as vinyl monomers. Examples of vinyl monomers which may be used to form the first and second phases of the multistage vinyl polymer include 1,3-butadiene, isoprene, styrene, a-methyl styrene, divinyl benzene, acrylonitronitrile, methacrylonitrile, vinyl halides such as vinyl chloride, vinyl esters such as vinyl acetate, vinyl propionate, vinyl laurate and vinyl esters of versatic acid such as VeoVa 9 and VeoVa 10 (VeoVa is a trademark of Shell), heterocyclic vinyl compounds, alkyl esters of mono-olefinically unsaturated dicarboxylic acids (such as di-n-butyl maleate and di-n-butyl fumarate) and, in particular, esters of (meth)acrylic acid of formula $CH_2=CR^1COOR^2$ wherein $R^1$ is H or methyl and $R^2$ is optionally substituted alkyl or cycloalkyl of 1 to 20 carbon atoms (more preferably 1 to 8 carbon atoms) examples of which are methyl(meth)acrylate, ethyl(meth)acrylate, butyl(meth)acrylate (all isomers), isobutyl(meth)acrylate, 2-ethylhexyl(meth)acrylate, isopropyl(meth)acrylate, propyl (meth)acrylate (all isomers) and hydroxyalkyl(meth)acrylates such as hydroxyethyl(meth)acrylate, 2-hydroxypropyl (meth)acrylate and their modified analogues like Tone M-100. (Tone is a trademark of Union Carbide Corporation). Olefinically unsaturated monocarboxylic and/or dicarboxylic acids, such as (meth)acrylic acid, beta carboxy ethylacrylate, fumaric acid and itaconic acid, are other examples which can be used.

Particularly preferred are vinyl polymers made from a monomer system comprising at least 60 wt % of one or more vinyl monomers of the formula $CH_2=CR^1COOR^2$ defined above, styrene, α-methyl styrene and acrylonitrile. Such preferred vinyl polymers are defined herein as (meth)acrylic polymers. More preferably, the vinyl monomer system contains at least 70 wt % of such monomers and particularly at least 80 wt %. The other monomers in such (meth)acrylic polymers (if used) may include one or more of the other vinyl monomers mentioned above and/or may include ones different to such other monomers. Most preferred monomers include methyl methacrylate, n-butyl(meth)acrylate, (meth) acrylic acid, styrene and 2-ethylhexyl acrylate.

The vinyl polymers may contain vinyl monomers, which provide an adhesion and/or crosslinking functionality to the resulting polymer coating. Examples of these include (meth) acrylic monomers having at least one free carbonyl, hydroxyl, epoxy, aceto acetoxy, or amino group; allyl methacrylate, tetraethylene glycol methacrylate and divinyl benzene. Adhesion promoting monomers include amino, urea, or N-heterocyclic groups. Such monomers, when used, are normally used in an amount of from 0 to 5 wt % and more usually from 0 to 2 wt % of the total weight of monomers used for polymerisation.

It will be appreciated that although the multistage vinyl polymer can be made from one or more of the above-discussed vinyl monomers, it will be necessary to select both the amounts and types of such monomers to provide the desired Tg characteristics.

The term vinyl polymer as used herein includes one vinyl polymer as well as more than one vinyl polymer.

The preparation of the vinyl polymer is executed so as to provide a multiphase polymer. The term multiphase is used to refer to any polymer constructions that allow combining polymers of different properties and/or morphologies into a single film-forming coating composition. These constructions include: oligomer-polymer constructs, a blend of two polymers, a sequential polymer (including core-shell) and combinations of the foregoing.

The multiphase vinyl polymer used in the primer preferably is a multistage vinyl polymer. This refers to a polymer system that has been formed by a multistage emulsion polymerisation process in which two or more polymer phases are prepared by the sequential aqueous emulsion polymerisation of two or more distinct monomer mixtures. Thus in its simplest and preferred form a first polymer phase is preferably formed by emulsion polymerisation, which could for example be either soft or hard as defined in the invention and then a second polymer phase is preferably formed by emulsion polymerisation in the presence of the first polymer phase; the second polymer could be soft if the first polymer is hard, or could be hard if the first polymer is soft. More complex multistage polymer designs include ones with two or more soft polymer phases and/or two or more hard polymer phases, the polymerisations being carried out in any order.

Preferably the multistage vinyl polymer comprises <10 wt %, more preferably 0.5 to 6 wt % and most preferably 2 to 5.5 wt % of vinyl monomers bearing ionic or potentially ionic water-dispersing groups.

Preferably the vinyl monomers bearing ionic or potentially ionic water-dispersing groups are vinyl monomers bearing anionic or potentially anionic water-dispersing groups, more preferably vinyl monomers bearing carboxylic acid groups and most preferably (meth)acrylic acid.

In a preferred embodiment a hard polymer phase (i) may be derived from a vinyl monomer composition comprising 40 to 100 wt % (more preferably 60 to 90 wt %) of at least one monomer selected from methyl methacrylate, styrene, ethyl methacrylate and acrylonitrile; 0 to 60 wt % (more preferably 10 to 40 wt %) of at least one monomer selected from n-butyl acrylate, n-butyl methacrylate, ethyl acrylate and 2-ethylhexyl acrylate; and 0 to 6 wt % (preferably 0.5 to 4.5 wt %) of at least one monomer selected from acrylic acid, methacrylic acid and beta carboxyethyl acrylate.

In a preferred embodiment a soft polymer phase (ii) may be derived from a vinyl monomer composition comprising 40 to 100 wt % (preferably 50 to 80 wt %) of at least one monomer selected from n-butyl acrylate, n-butyl methacrylate, ethyl acrylate and 2-ethylhexyl acrylate; 0 to 60 wt % (preferably 20 to 50 wt %) of at least one monomer selected from methyl methacrylate, styrene, ethyl methacrylate and acrylonitrile; and 0 to 6 wt % of at least one monomer selected from acrylic acid, methacrylic acid and beta carboxyethyl acrylate.

It is desired for the polymers making up the coating composition used in the primer of the invention to have a moderate acid value. Preferably each phase has from 2 to 10 wt % of carboxylic acid functional monomers based on the total amount of monomers.

Preferably the multiphase polymer (overall) has from 2.5 to 10 wt % of carboxylic acid functional monomers, based on the total amount of monomers.

Preferably the acid value is between 10 mg and 70 mg KOH/g polymer, more preferably between 30 mg and 50 mg KOH/g polymer.

The multiphase polymer used in the primer preferably forms relatively small particles. Generally the average particle size will be below 500 nm. The average particle size preferably is below 400 nm, more preferably below 300 nm, and most preferably below 150 nm.

The particles size refers to the average particle diameter or size as determined by light scattering using a Malvern Zeta sizer 3000 HSa.

In making the multiphase polymers used in the present invention, customary polymerization methods can be used, including processing adjuvants such as initiators, chain transfer agents, and surfactants.

The vinyl polymers used in the invention composition are normally made using free radical addition polymerisation in an aqueous emulsion polymerisation process to form an aqueous polymer emulsion. Such an aqueous emulsion polymerisation process is, in itself, well known in the art and need not be described in great detail. Suffice to say that such a process involves dispersing the vinyl monomers in an aqueous medium and conducting polymerisation using a free-radical yielding initiator and (usually) appropriate heating (e.g. 30 to 120° C.) and agitation (stirring) being employed. The aqueous emulsion polymerisation can be effected using one or more commonly used surfactants. Anionic and non-ionic surfactants and combinations of the two types are preferred. Chain transfer agents (e.g. mercaptanes or suitable cobalt chelate complexes) may be included if desired to control molecular weight.

Suitable free-radical-yielding initiators include inorganic peroxides such as K, Na or ammonium persulphate, hydrogen peroxide, or percarbonates; organic peroxides, such as acyl peroxides including e.g. benzoyl peroxide, alkyl hydroperoxides such as t-butyl hydroperoxide and cumene hydroperoxide; dialkyl peroxides such as di-t-butyl peroxide; peroxy esters such as t-butyl perbenzoate and the like; mixtures may also be used. The peroxy compounds are in some cases advantageously used in combination with suitable reducing agents (redox systems) such as Na or K pyrosulphite or bisulphite and iso-ascorbic acid. Metal compounds such as Fe.EDTA (EDTA is ethylene diamine tetracetic acid) may also be usefully employed as part of the redox initiator system. Azo functional initiators may also be used. Preferred azo initiators include azobis(isobutyronitrile) and 4,4'-azobis(4-cyanovaleric acid). The amount of initiator or initiator system used is conventional, e.g. within the range 0.05 to 4 wt % based on the total vinyl monomers used. Preferred initiators include ammonium persulphates, sodium persulphates, potassium persulphates, azobis(isobutyronitrile), 4,4'-azobis(4-cyanovaleric acid) and/or t-butyl hydroperoxide.

Suitable chain transfer agents include mercaptans such as n-dodecylmercaptan, n-octylmercaptan, t-dodecylmercaptan, mercaptoethanol, iso-octyl thioglycolate, $C_2$ to $C_8$ mercapto carboxylic acids and esters thereof such as 3-mercaptopropionic acid and 2-mercaptopropionic acid; and halogenated hydrocarbons such as carbon tetrabromide and bromotrichloromethane. Preferably ≤5 wt %, more preferably ≤3 wt % and most preferably no chain transfer agent based on the weight of vinyl monomers required is used.

The amount of surfactant used in the emulsion polymerisation to make a multistage polymer is preferably 0.25 to 5 wt % based on the total weight of monomers used for the first and second phase polymers of the multistage polymer, more preferably 0.5 to 3 wt % and particularly 1 to 2 wt %.

Preferably, the amount of free monomers in the coating composition is lower than 500 ppm, preferably lower than 200 ppm, more preferably lower than 100 ppm.

The primer coating composition comprising the multiphase vinyl polymer described hereinbefore is employed as a primer on a metal wire. This means that the primer coating composition concerned is the first layer, applied directly onto the metal. The fact that the coating composition is used as a primer also means that the primer layer does not form the eventual outer surface of the wire.

Before application of the primer the metal wire can be pretreated, for instance by using the methods described in ASTM A967 or ASTM A380.

The outer surface is, as indicated above, a topcoat. Any topcoat suitable for medical application can be used, e.g. coatings serving anti-microbial or anti-thrombogenic properties. Particularly, the topcoat is a lubricious hydrophilic topcoat.

It is conceivable that either or both of the primer and the topcoat are present in more than one layer. It is also conceivable that a further coating composition, different from the primer and the topcoat, is applied as an intermediate coating between the one or more primer layers and the one or more topcoat layers. It is also possible to blend the primer coating composition with other polymer solutions or dispersions before application as the primer layer onto the metal. This, however, is not preferred as one would risk losing one of the benefits of using the primer of the invention, viz. the favourable property of giving a good adhesion to both the metal of the wire and the topcoat. Also, the elastic, the cohesive, and other material properties of the intermediate coating should match those of the primer if one were to retain all of the primer's advantages, including flexibility. Hence, it is preferred that the full coating applied on to the metal wire consists essentially of the primer (in one or more layers of a multiphase vinyl polymer coating composition as described above) and the topcoat.

The topcoat generally is made of an aqueous solution of a water-soluble hydrophilic polymer. Examples of suitable hydrophilic polymers are:
(1) homopolymers or copolymers of acrylates, methacrylates, acrylonitrile, acrylamide, such as polyacrylamide products commercially available under the trade names "Separan", "Purifloc", "Magnafloc" and "Hercules", acrylic acid, such as polyacrylic acid products commercially available under the trade names "Carbopol", "Versicol" and "Primal", and methacrylic acid.
(2) carboxymethyl cellulose,
(3) copolymers of maleic acid anhydride and vinyl ether, such as a product commercially available under the trade name "Gantrex",
(4) polysaccharides, such as dextran.

The topcoat can be of a radiation curable type. The radiation used can be gamma radiation, electron beam radiation, ultra-violet (UV) radiation or near-infrared radiation (NIR). Preferably the topcoat is radiation curable, more preferably UV curable eg NeoRad series from DSM NeoResins BV eg NeoRad R440 [UV curable, aliphatic urethane dispersion, MFT<4° C.].

The topcoat can be formed from an aqueous or alcoholic (e.g. methanol, ethanol, isopropanol) or aqueous alcohol mixtures of solution or dispersion of a hydrophilic polymer having organic acid functional groups, a second polymer having organic acid functional groups, and a second polyfunctional crosslinking agent having functional groups being capable of reacting with organic acid groups. This composition is dried to effectuate covalent bonding of the hydrophilic polymer and the second polymer to the first polymer of the first coating composition through the first or the second crosslinking agents to form a unitary hydrophilic topcoat. Hydrophilic polymers may also be selected from a wide variety of polymers which can be covalently bonded to different coating compositions due to the presence of their organic acid functionality. Of particular preference are the polyacrylic acid polymers and the acrylamide-acrylic acid copolymers, and these hydrophilic polymers should be near or at the exterior surface of the coating to provide lubricity thereat. When dried these hydrophilic polymers become lubricious upon contact with an aqueous solution. The hydrophilic polymer may comprise monomer units from one or more monomers having organic acid functional groups. Preferred examples of such monomers include acrylic acid, methacrylic acid and isocrotonic acid. In addition to comprising monomer units from at least one monomer having organic acid functional groups, the hydrophilic polymer may contain monomer units from at least one hydrophilic monomer without any organic acid functional groups, such as vinylpyrrolidone and acrylamide. A preferred example of a copolymer for use in or as the hydrophilic polymer in the method according to the present invention is an acrylic acid-acrylamide copolymer. The acrylamide-acrylic acid copolymer supplied by Allied Colloids under the tradenames Versicol and Glascol. Versicol WN 23 and Glascol WN 33 are specific examples of such copolymers. The hydrophilic polymer is preferably present in the aqueous solution in a concentration of from 0.5 to 5 percent by weight and typically of about 1.25 percent by weight.

Most preferably the topcoat is a UV curable coating composition based on polyvinylpyrrolidone (PVP). Suitable UV curable topcoats include those described in WO2006/056482, WO2008/104573, EP1957130 and WO2009/112548.

The primer can be applied using techniques as generally known in the art. For example, this is done by dip, spray or flow coating equally by brushing, wiping, swabbing or similar application methods. Preferably this is done by dip coating. It is advisable to first de-grease the metal substrate, e.g. by cleansing it with, for instance, acetone. The metal surface can also be passivated according to a process known to the person skilled in the art. After application of the primer a drying step will follow before application of the topcoat so as to at least partially dry the primer up to a level of being touch-dry. The drying preferably is in air, at room temperature or elevated temperature. The temperature typically is less than 70° C.

The primer is preferably applied with a layer thickness within the range of from 500 nm to 200 μm. A preferred layer thickness ranges from 1 μm to 20 μm.

The topcoat can be applied using techniques as generally known in the art. Preferably this is done by dip-coating. The topcoat is cured e.g. by UV irradiation or by heat.

The resulting coating system, comprising primer and topcoat, provides the right combination of properties for the coating of metal wires, and particularly of coiled wires. Representative properties, such as lubricity and flexibility, can be determined in a friction test.

A low friction is of particular importance for wires used in cardiovascular applications in human bodies. It is therefore preferred the coated wire is extremely smooth, i.e. as low a friction as possible, to prevent infections and damage to the blood vessels or other tissue.

To be suitable for use on coiled wires, the coating system should be very flexible.

For application in human or animal bodies, it will be understood that the coating system should be acceptable from a regulatory point of view.

As a result of the primer of the invention, the coating system as described hereinbefore can be applied so as to provide adhesion on metal wires.

The invention also relates to a coated metal wire as obtainable by the method according to the invention and a medical device, particularly a catheter or a guide wire provided with a coating as obtainable by the method according to the invention.

The coated metal wires as described according to the invention can be used in any medical device, including components of medical devices, in which metal wires are normally used, such as a guidewire, a stent or a tube. In view of the good lubricity of the topcoat combined with the favourable adhesion, cohesive strength, and flexibility provided by the primer, the devices of the invention are particularly suitable for use in cardiovascular medicine, particularly coronary angioplasty, or in neurointerventional catheterization.

In summary, a method is described to provide a metal wire with a coating system comprising a primer and a hydrophilic, lubricious topcoat. The method comprises applying directly onto the wire metal a primer coating composition, which is an aqueous coating composition comprising a multiphase vinyl polymer, the polymer comprising a first phase having a Tg in the range of from −20° C. to 40° C. and a second phase having a Tg in the range of from 25° C. to 120° C. The primer has good adhesion to both the metal surface and the topcoat, and provides the eventual coating system with, inter alia, a good flexibility.

To various aforementioned parameters and tests conducted, the following standards apply:

The friction test was conducted using a method based on ISO 11070:1998(E), annex F (Sterile single-use intravascular catheter Introducers).

The Tg was determined according to ISO 11357-2 with DSC.

Minimum film forming temperature (MFFT) was measured according to the ISO 2115:1996(E).

Friction measurement is performed using a test that can be described as follows: The test is performed using a reciprocal movement at a constant velocity of 1 cm/s with plane-cylinder contact as described by ISO 6601:2002 (E). The test is performed against a counter surface of silicone (60 Durometer) submersed in de-ionised water at room temperature. The normal load is fixed for a given experiment, but may take any value from 1N to 10N.

The bend test was performed based on ISO 1170: 1998 (E), annex F by winding the coated guidewire eight times around a cylinder. The cylinder was 10 times the maximum wire diameter. The smaller radius bend test was performed by using a cylinder that was 5 times the maximum wire diameter.

The invention will be illustrated with reference to the following, non-limiting examples.

EXAMPLE 1

Two emulsified monomer feeds were prepared. Monomer feed 1 was prepared by mixing water (165.5 g), sodium bicarbonate (0.7 g), Surfagene® FAZ 109V (50.9 g) (a surfactant), acrylic acid (30.7 g), butyl acrylate (175.2 g), butylmethacrylate (374.6 g), methylmethacrylate (32.8 g). Monomer feed 2 was prepared by mixing water (103.9 g), sodium bicarbonate (0.5 g), Surfagene® FAZ 109V (29.3 g), acrylic acid (13.1 g), butylmethacrylate (188.1 g), methylmethacrylate (61.5 g). An initiator feed was prepared by mixing water (48.7 g), ammonium persulphate (2.6 g), sodium bicarbonate (0.4 g) and Surfagene® FAZ 109V (17.9 g). Monomer feed 1 makes up 76 wt. % of the vinyl polymer and monomer feed 2 makes up 24 wt. % of the vinyl polymer.

A 2 liter three-neck round bottom glass reactor, equipped with a stirrer, nitrogen inlet, thermometer and baffles was loaded with water (582.7 g), sodium bicarbonate (0.5 g), Surfagene® FAZ 109V (41.9 g), and ammonium persulphate (0.5 g).

The temperature of the reactor phase was raised to 90° C., 10% of the monomer feed 1 was added. Then, 67% of the initiator feed as well as the total monomer feed 1 were added over 50 minutes to the reactor. After addition of monomer feed 1 was completed, the reaction mixture was kept at 90° C. for 15 minutes. Subsequently, monomer feed 2 as well as the remaining initiator feed were added over 25 minutes to the reactor. After addition of both feeds was completed, the reaction mixture was kept at 90° C. for 30 minutes followed by cooling to room temperature. If necessary at this stage t-butylhydroperoxide and i-acrylic acid were employed at 85° C. to consume any remaining monomers. The pH was adjusted using a 25% ammonia solution. Finally, the reaction mixture was filtered and collected as a polymer latex. The final polymer has a pH of 5.5, a viscosity of 200 mPa·s, a solids content of 46% and was prepared with a coagulum below 0.10%. The average particle size was 99 nm and the calculated Tg of the vinyl polymer formed from feed 1 was 0° C. and the calculated Tg of the vinyl polymer formed from feed 2 was 40° C.

COMPARATIVE EXAMPLE 2

An emulsified monomer feed was prepared by mixing water (269.4 g), sodium bicarbonate (1.2 g), Surfagene® FAZ 109V (80.2 g), acrylic acid (43.8 g), butyl acrylate (175.2 g), butylmethacrylate (438 g), methylmethacrylate (219 g). An initiator feed was prepared by mixing water (69.2 g), ammonium persulphate (2.6 g), sodium bicarbonate (0.4 g) and Surfagene® FAZ 109V (17.9 g).

A 2 liter three-neck round bottom glass reactor, equipped with a stirrer, nitrogen inlet, thermometer and baffles was loaded with water (582.7 g), sodium bicarbonate (0.5 g), Surfagene® FAZ 109V (41.9 g), and ammonium persulphate (0.5 g).

The temperature of the reactor phase was raised to 90° C., and 10% of the monomer feed was added. Then, the initiator feed as well as the monomer feed were added over 75 minutes to the reactor. After addition of the monomer feed was completed, the reaction mixture was cooled to room temperature. If necessary at this stage t-butylhydroperoxide and i-acrylic acid were employed at 85° C. to consume any remaining monomers. The pH was adjusted using a 25% ammonia solution. Finally, the reaction mixture was filtered and collected as a polymer latex. The final polymer has a pH of 5.5, a viscosity of 200 mPa·s, a solids content of 46% and was prepared with a coagulum below 0.10%. The average particle size was 120 nm and the calculated Tg based on the overall monomer composition was 20° C.

EXAMPLE 3

The substrate, a 0.20×0.69×400 mm stainless steel 304 coiled wire containing a 0.2 mm straight core was dipped in the primer, soaked for 10 s and withdrawn at a constant rate of 1 cm/s, the coated device was then allowed to dry at room temperature.

Properties of the applied primer are tabulated below (table 1). A topcoat formulation as described below was then applied by dip coating at 1 cm/s draw speed, allowed to air dry and cured by UV-VIS irradiation for 360 s.

Coating Formulation for the Topcoat:

| Compound | Amount (wt %) |
| --- | --- |
| PVP (Kollidon 90F, BASF) | 3.4 |
| Irgacure 2959 | 0.01 |
| Benzophenone | 0.1 |
| PEG1500 diacrylamide | 0.3 |
| Tween 80 | 0.04 |
| Ethanol 96% | 96.2 |

PEG1500 diacrylamide was prepared as described in WO2009/112548.

The coated samples were then evaluated according to the bend test described according to ISO 11070:1998(E), annex F around the specified radius (4.5 mm) and a smaller radius (2 mm) and according to a friction test performed using a reciprocal movement at a constant velocity of 1 cm/s with plane-cylinder contact as described by ISO 6601:2002(E). The test was performed against a counter surface of silicone rubber (60 Durometer) submersed in de-ionised water at room temperature with a normal load of 6 N.

The Primers, as tabulated (table 1) were produced in the same manner as those in example 1, the man skilled in the art is able to select suitable monomer combinations to achieve the specified properties by computing the Tg according to the method described in the text.

Primer 2 corresponds to the primer prepared according to Example 1 and Primer 12 corresponds to the primer prepared according to Comparative Example 2.

TABLE 1

Primer coating specification

| Primer Number | modification | % carboxylic acid | Tg phase 1 (° C.) | Tg phase 2 (° C.) | phase ratio (wt. %) |
| --- | --- | --- | --- | --- | --- |
| 1. | % acid | 2.5 | 0 | 80 | 70/30 |
| 2. | % acid | 5.0 | 0 | 80 | 70/30 |
| 3. | % acid | 7.5 | 0 | 80 | 70/30 |
| 4. | Phase ratio 80/20 | 5 | 0 | 80 | 80/20 |
| 5. | Phase ratio 60/40 | 5 | 0 | 80 | 60/40 |
| 6. | Tg variation | 5 | −10 | 80 | 70/30 |
| 7. | Tg variation | 5 | 0 | 100 | 70/30 |
| 8. | Tg variation | 5 | 0 | 60 | 70/30 |
| 9. | Tg variation | 5 | 0 | 40 | 70/30 |
| 10. | Only low Tg phase | 5 | 0 | — | 100/0 |
| 11. | Only high Tg phase | 5 | — | 80 | 0/100 |
| 12. | average polymer | 5 | 20 | — | n/a |

The phase ratio is that of phase 1 to phase 2

TABLE 2

Results of testing on lubricious topcoat applied to primers from table 1; evaluation of combined layers.

| Primer number | Friction test (6N) | Bend test | Bend test smaller radius | Appearance after test | Overall performance |
| --- | --- | --- | --- | --- | --- |
| 1 | Good | Small fibrils | Fibrils | Poor | o.k. |
| 2 | Good | ok | Cracks | ok | good |
| 3 | Good | ok | Small fibrils | Good | o.k. |
| 4 | Good | Good | Good | Good | good |
| 5 | Good | Some fibrils/ok | Some fibrils | Moderate | o.k. |
| 6 | Good | Good | Good | Moderate | o.k |
| 7 | Good | Good | Good | Good | good |
| 8 | Good | Good | Good | Poor | o.k. |
| 9 | Good | Good | Good | Good | good |
| 10 + 11 mix | Good | Good | Some delamination | Good | poor |
| 12 | marginal | Some fibrils | Some fibrils/ok | Moderate | poor |

Overall performance was determined by considering the combined impact of the friction test, with both the small and large radius bend tests.

The invention claimed is:

1. A method for providing a metal wire with a coating system comprising at least a primer and a topcoat, the method comprising:
   I) applying directly onto the metal wire a primer coating composition, and allowing the primer to at least partially dry:
   II) applying a topcoat coating composition;
   III) curing the topcoat; wherein
   the primer coating composition is an aqueous composition having a minimum film forming temperature of below 40° C., comprising a multiphase vinyl polymer, comprising a first phase having a Tg in the range of from −20° C. up to 40° C., and a second phase having a Tg in the range of from 25° C. to 120° C., with the Tg of the second phase being higher than the Tg of the first phase.

2. A method according to claim 1, wherein the multiphase vinyl polymer is a multistage polymer formed by a multistage emulsion polymerisation process in which two or more polymer phases are prepared by a sequential aqueous emulsion polymerization of two or more distinct monomer mixtures.

3. A method according to claim 1, wherein the multiphase vinyl polymer is a (meth)acrylic polymer.

4. A method according to claim 1, wherein the difference in Tg between the two phases in the multiphase polymer is at least 20° C.

5. A method according to claim 1, wherein the first phase makes up 50 wt. % to 95 wt. % of the multiphase vinyl polymer, and the second phase makes up 5 wt. % to 50 wt. % of the multiphase polymer.

6. A method according to claim 1, wherein the multiphase vinyl polymer has from 2.5 wt. % to 10 wt. % of carboxylic acid functional monomers, based on the total amount of monomers.

7. A method according to claim 6, wherein the multiphase vinyl polymer has an acid value between 10 mg and 70 mg KOH/g polymer.

8. A method according to claim 1, wherein the multiphase vinyl polymer comprises particles having an average particle size below 500 nm.

9. A method according to claim 1, wherein the topcoat is radiation curable.

10. A method according to claim 1, wherein the topcoat coating composition upon curing results in a lubricious, hydrophilic topcoat.

11. A method according to claim 1, wherein the metal wire is a coiled wire.

12. A method according to claim 1, wherein the metal is stainless steel.

13. The method of claim 1 wherein the first phase has a Tg in the range of from −20° C. to 25° C., and the second phase has a Tg in the range of from 40° C. to 120° C.

14. The method of claim 1 wherein the difference in Tg between the two phases is 50° C. to 100° C.

15. A coated metal wire provided with a multilayer coating system comprising at the outer surface a hydrophilic, lubricious topcoat, and at the metal surface a primer comprising a multiphase vinyl polymer obtained by the method according to claim 1.

16. A medical device comprising a coated metal wire according to claim 15.

* * * * *